United States Patent [19]

Van Loveren et al.

[11] Patent Number: 4,559,168

[45] Date of Patent: Dec. 17, 1985

[54] USE OF MACROCYCLIC LACTONE IN AUGMENTING OR ENHANCING AROMA OR TASTE OF CONSUMABLE MATERIALS

[75] Inventors: Augustinus G. Van Loveren, Rye, N.Y.; Marie R. Hanna, Hazlet, N.J.; Domenick Luccarelli, Jr., Neptune, N.J.; David R. Bowen, Red Bank, N.J.; Manfred H. Vock, Locust, N.J.; Wilhelmus J. Wiegers, Red Bank, N.J.

[73] Assignee: International Flavors & Fragrances Inc., New York, N.Y.

[21] Appl. No.: 698,833

[22] Filed: Feb. 6, 1985

Related U.S. Application Data

[62] Division of Ser. No. 617,584, Jun. 5, 1984, which is a division of Ser. No. 514,523, Jul. 18, 1983, Pat. No. 4,490,404.

[51] Int. Cl.$^4$ ............................ A61K 7/46; C11B 9/00
[52] U.S. Cl. ................................................. 252/522 A
[58] Field of Search ..................................... 252/522 A

[56] References Cited

U.S. PATENT DOCUMENTS 4,379,071 4/1983 Schnöring et al. ............. 252/522 A
4,490,544 12/1984 Wiegers et al. ................. 252/522 R Primary Examiner—Helen M. S. Sneed
Attorney, Agent, or Firm—Arthur L. Liberman

[57] ABSTRACT

Described for use in augmenting or enhancing the aroma or taste of consumable materials including perfume compositions, colognes and perfumed articles, foodstuffs, chewing gums, toothpastes and medicinal products are the cis and/or trans isomers of the macrocyclic lactone defined according to the structure:

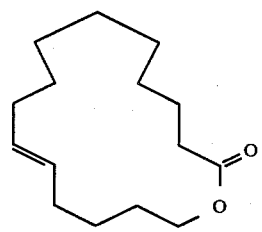

produced according to the process of first reacting the ester defined according to the structure:

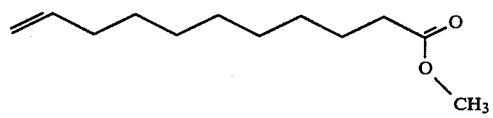

with the alkenol having the structure:

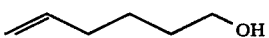

in order to produce the di-unsaturated ester having the structure:

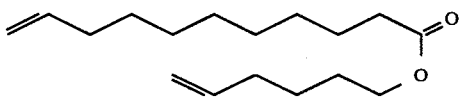

and then causing the said diester to undergo an internal metathesis to form the compound having the structure:

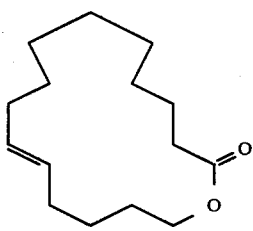

1 Claim, 9 Drawing Figures

NMR SPECTRUM FOR EXAMPLE I

GLC PROFILE FOR EXAMPLE II.

FIG.6 NMR SPECTRUM FOR EXAMPLE II (CIS ISOMER)

USE OF MACROCYCLIC LACTONE IN AUGMENTING OR ENHANCING AROMA OR TASTE OF CONSUMABLE MATERIALS

This is a divisional of application Ser. No. 617,584, filed June 5, 1984, which, in turn, is a divisional of application for U.S. Letters Patent, Ser. No. 514,523 filed on July 18, 1983, now U.S. Pat. No. 4,490,404 issued Dec. 25, 1984.

BACKGROUND OF THE INVENTION

This invention relates to the use of the macrocyclic lactone having the structure:

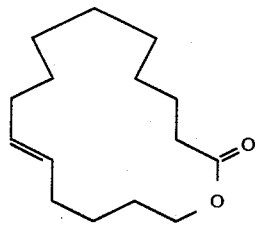

in augmenting or enhancing the aroma or taste of consumable materials including perfume compositions, colognes, perfumed articles, foodstuffs, chewing gums, toothpastes and medicinal products.

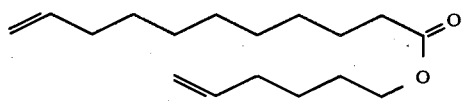

(conditions: Field Strength: 100 MHz; Solvent: CFCl$_3$).

Figure 2:
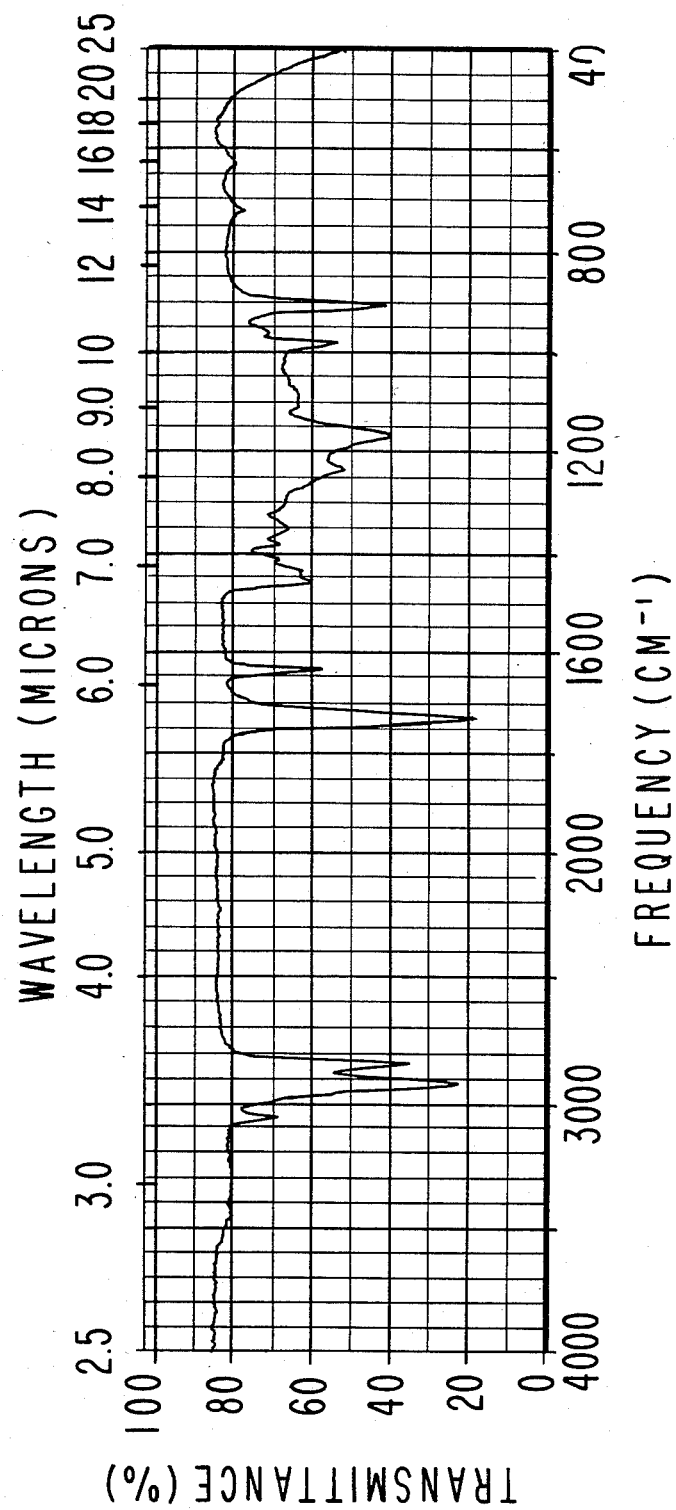

FIG. 2 is the infra-red spectrum for the compound having the structure:

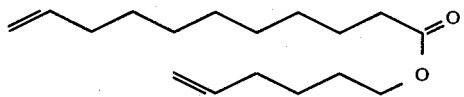

produced according to Example I.

Figure 3:
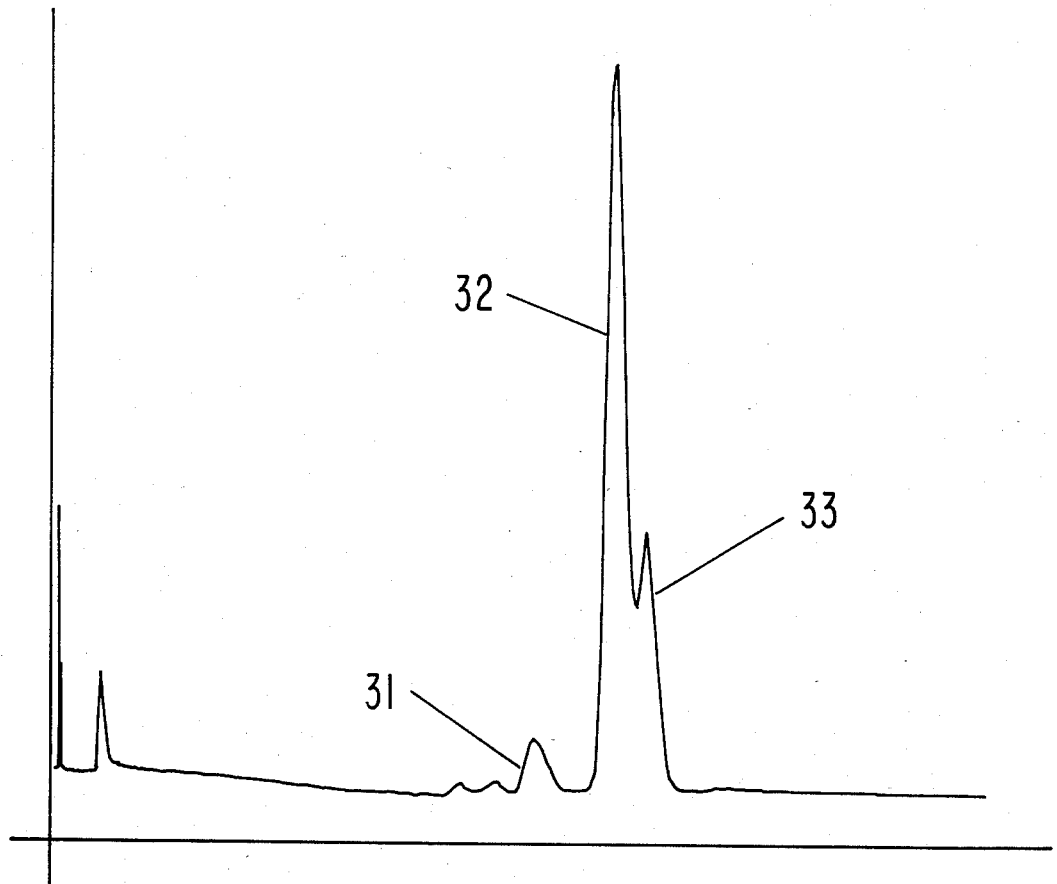

FIG. 3 is the GLC profile for the reaction product of Example II containing the compound having the structure:

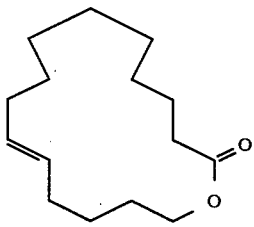

(conditions: 10% Carbowax column, 10'×0.25" programmed at 150°-225° C. at 8° C. per minute).

Figure 4:
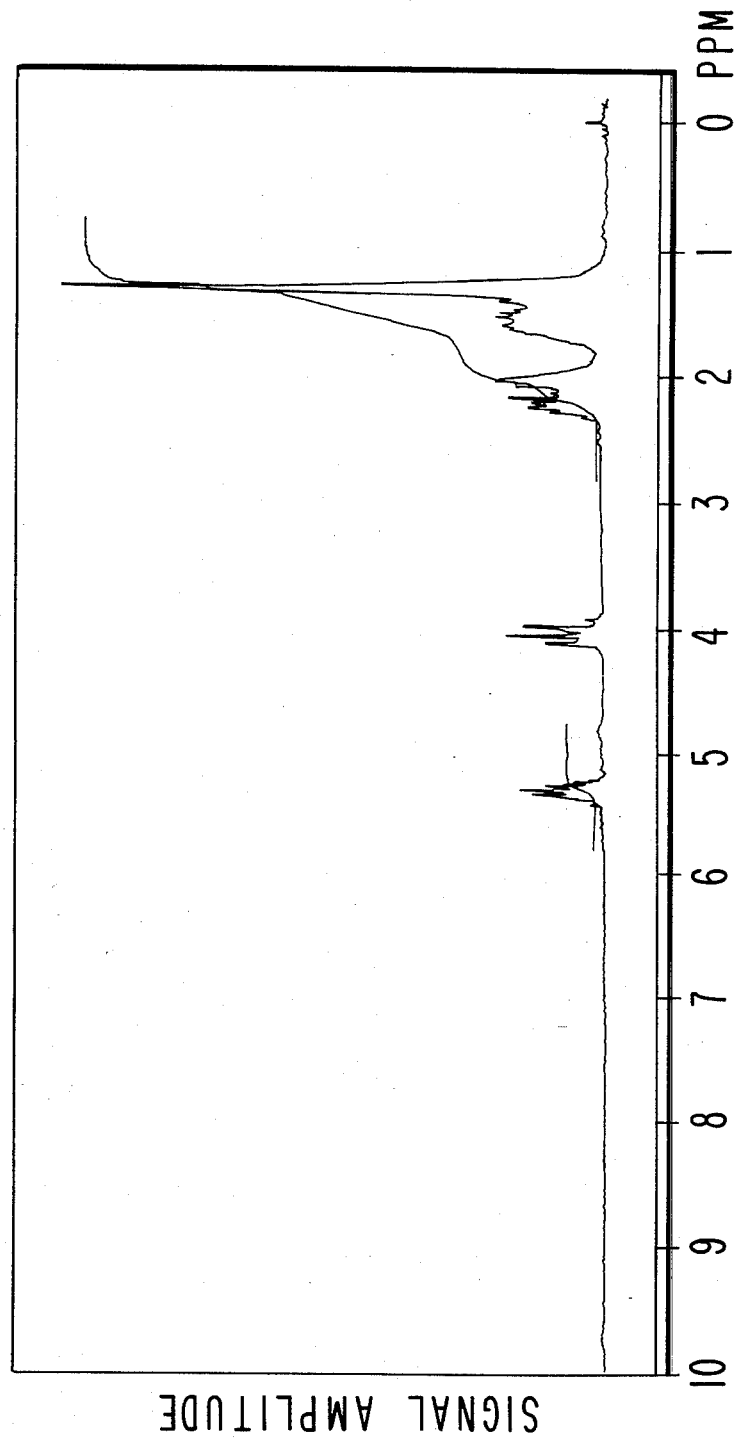

FIG. 4 is the NMR spectrum for the trans isomer of the compound having the structure:

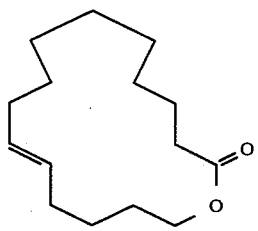

produced according to Example II (conditions: Field strength: 100 MHz; Solvent: CFCl$_3$).

Figure 5:
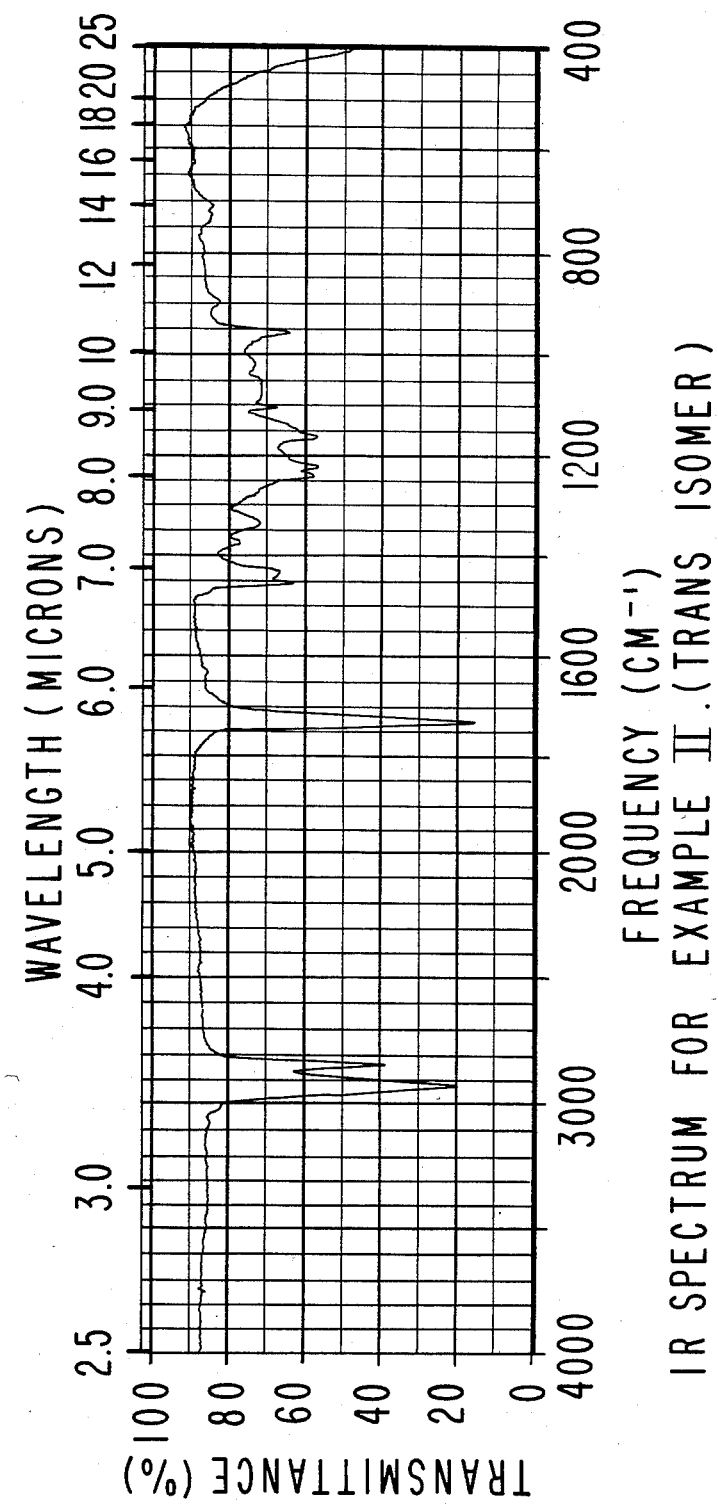

FIG. 5 is the infra-red spectrum for the trans isomer of the compound having the structure:

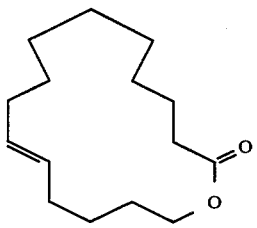

produced according to Example II.

Figure 6:
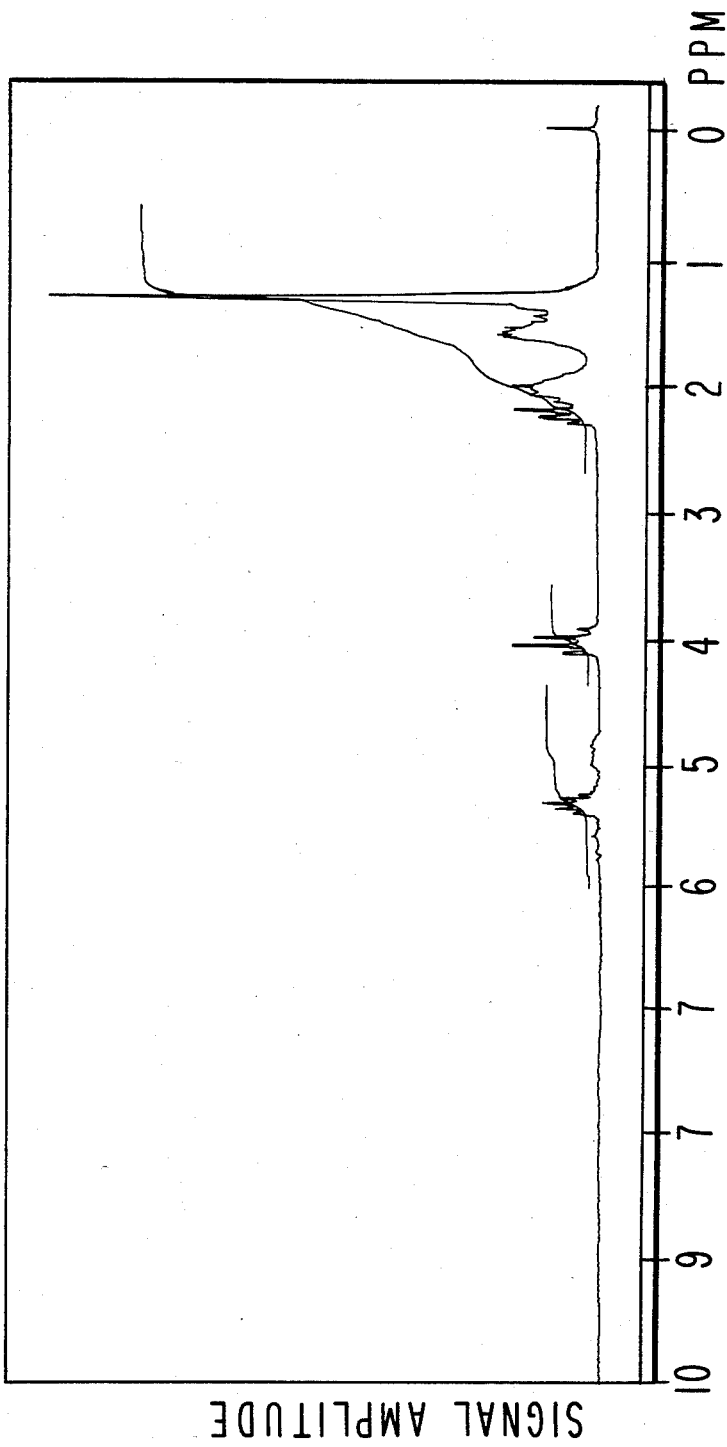

FIG. 6 is the NMR spectrum for the cis isomer of the compound having the structure:

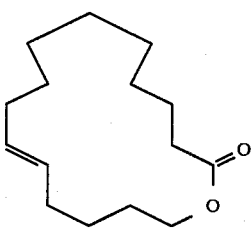

produced according to Example II (conditions: Field Strength: 100 MHz; Solvent: CFCl$_3$).

Figure 7:
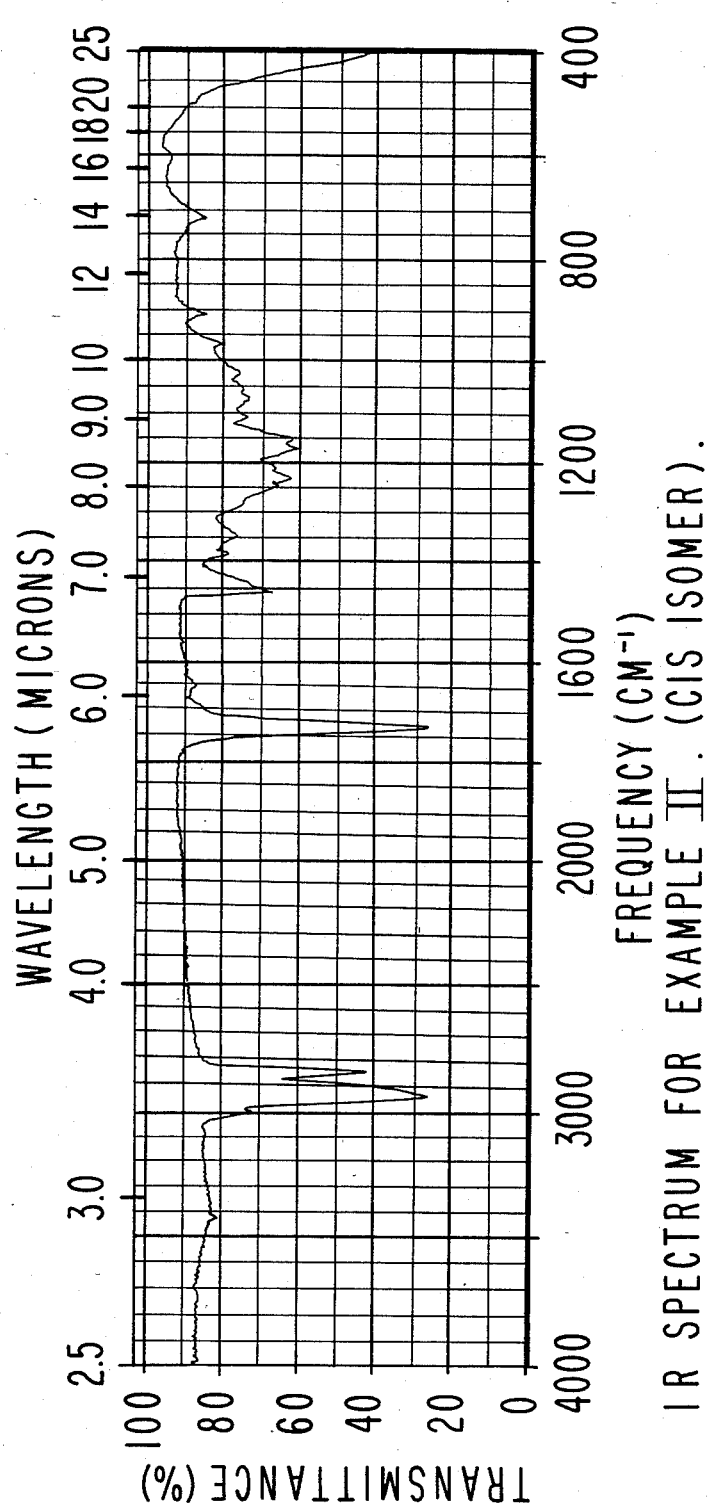

FIG. 7 is the infra-red spectrum for the cis isomer of the compound having the structure:

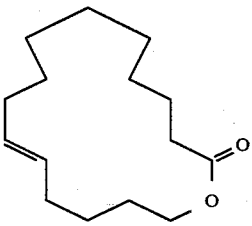

produced according to Example II.

Figure 8:
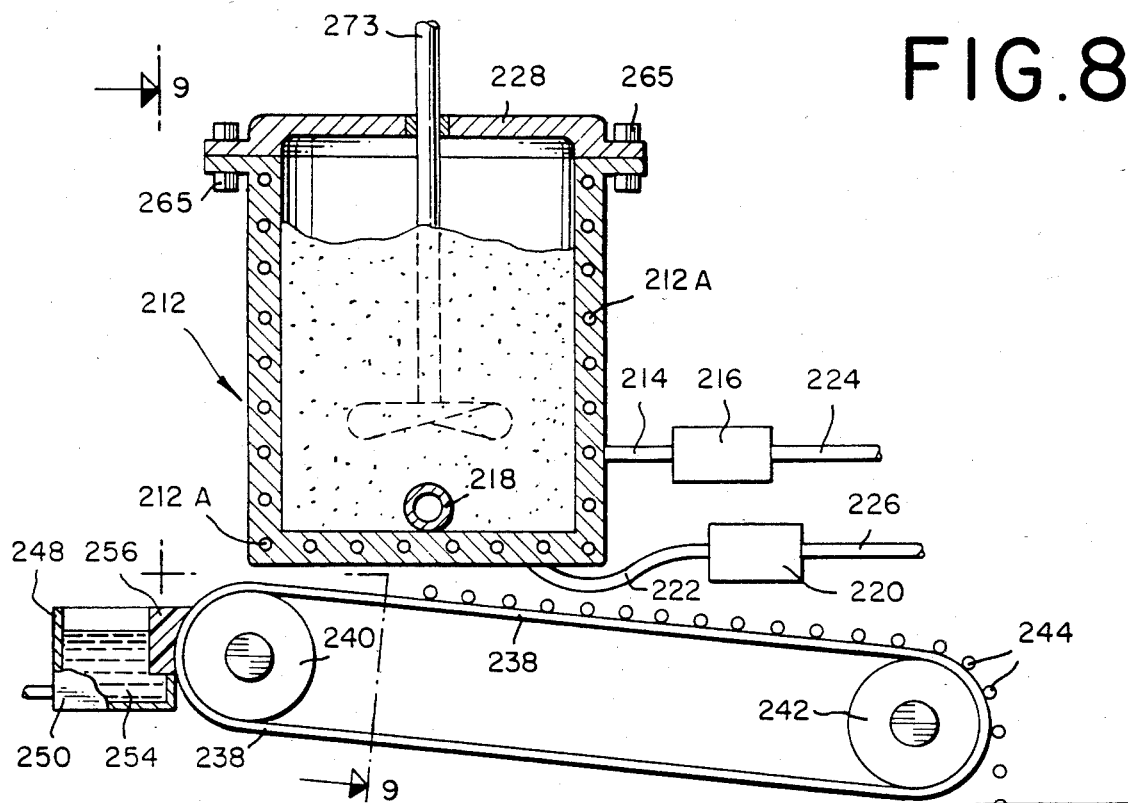

FIG. 8 is a partial side elevation and partial sectional view of an apparatus for forming scented polymer using the compounds defined according to the structure:

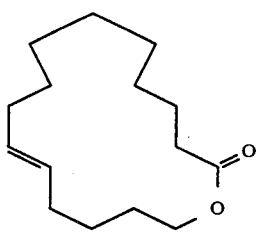

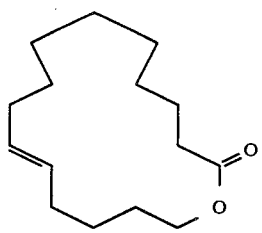

constructed in accordance with the invention.

Figure 9:
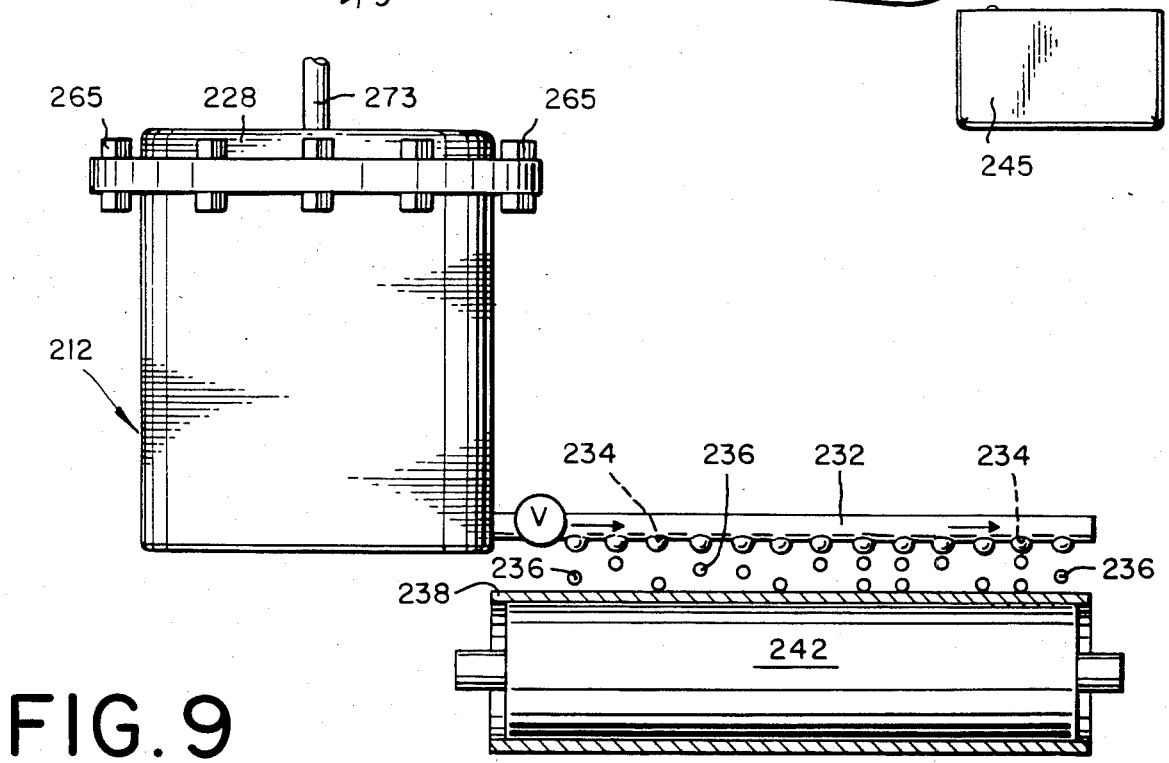

FIG. 9 is a section taken along line 9—9 of FIG. 8.

DETAILED DESCRIPTION OF THE DRAWINGS

FIG. 3 is the GLC profile for the reaction product of Example II (conditions: 10′×0.25″ 10% Carbowax column programmed at 150°–225° C. at 8° C. per minute). The peak indicated by reference numeral "31" is the peak for the starting material having the structure:

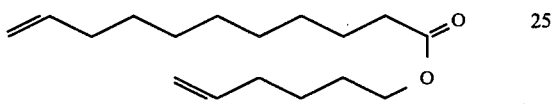

The peak indicated by reference numeral "32" is the peak for the trans isomer of the compound having the structure:

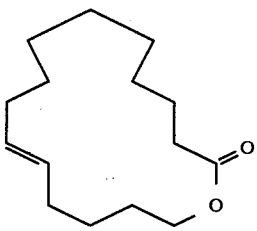

The peak indicated by reference numeral "33" is the peak for the cis isomer of the compound having the structure:

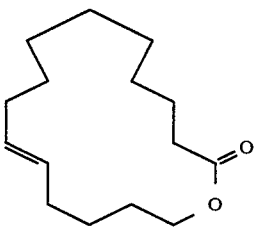

Referring to the drawings in FIGS. 8 and 9 in particular, the invention embodied therein comprises a device for forming scented polymer pellets (e.g. polyethylene, polypropylene or mixtures of polyepsilon caprolactone and polyethylene or polypropylene or co-polymers of polyvinyl acetate and polyethylene) which comprises a vat or container 210 into which a mixture of polymer such a polyethylene and the cis and/or trans compound defined according to the structure:

or a mixture of perfume materials including as a key ingredient one or both of the isomers defined according to the structure:

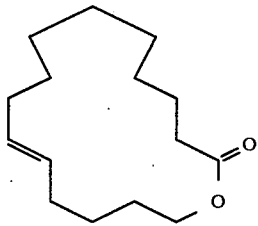

is placed.

The container is closed by an air tight lid 228 clamped to the container by clamps 265. A stirrer 273 traverses the lid or cover 228 in air tight manner and is rotated in a suitable manner. A surrounding cylinder 212 having heating coils which are supplied with electrical current through cable 214 from a rheostat or control 216 is operated to maintain the temperature inside the container 210 such that the polymer such as polyethylene in the container will be maintained in the molten or liquid state. It has been found advantageous to employ colorless, odorless polymer such as low-density polyethylene with a viscosity ranging between 180 and 220 centistokes and having a melting point in the neighborhood of 220° F. The heater 212 is operated to maintain the upper portion of the container 210 within the temperature range of from 250°–350° F. An additional bottom heater 218 is regulated through a control 220 connected thereto through a connecting wire 222 to maintain the lower portion of the container 210 within a temperature range of from 250°–350° F.

In accordance with this aspect of the invention, a polymer such as polyethylene or polypropylene is added to the container 210 and is then heated from 10 to 12 hours whereafter a scent or aroma imparting material containing the compound having the structure:

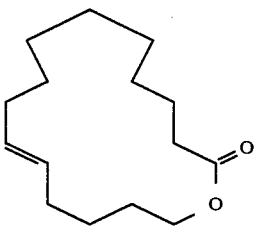

is quickly added to the melt. The material must be compatible with the polymer and forms a homogeneous liquid melt therewith. The heat resisting mixture, generally about 10–40% by weight of material having the structure:

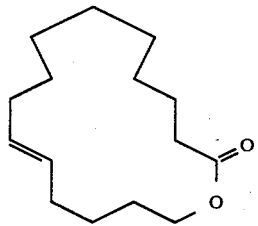

or mixture containing such compound or isomer is added to the polymer.

After the compound having the structure:

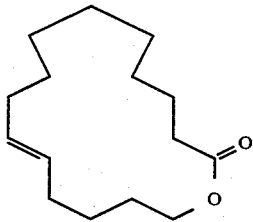

or mixture containing same is added to container 210, the mixture is stirred for a few minutes, for example 5–15 minutes, and maintained within the temperature ranges indicated previously by the heating coils 212 and 218 respectively. The controls 216 and 220 are connected through cables 224 and 226 to a suitable supply of electric current for supplying the power for heating purposes.

Thereafter the valve "V" is opened permitting the mass to flow outwardly through a conduit 232 having a multiplicity of orifices 234 adjacent the lower side thereof. The outer end of the conduit 232 is closed so that the liquid polymer and substance containing compound having the structure:

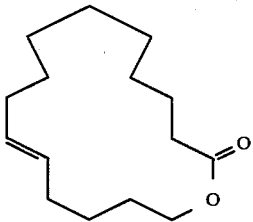

will continuously drop through the orifice 234 downwardly from the conduit 232. During this time the temperature of the polymer and the compound having the structure:

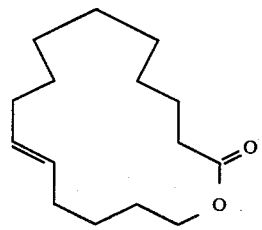

or mixture containing same in the container 210 is accurately controlled so that a temperature in the range of from 210° F. up to 275° F. will exist in the substance exiting in the conduit 232. The regulation of the temperature through the control 216 and the control 220 is essential in order to insure temperature balance to provide for the continuous dropping or dripping of molten polymeric material having the structure:

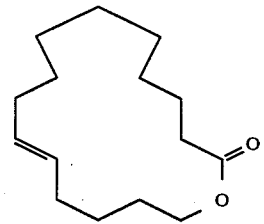

or mixture containing same through the orifices 234 at a range which will insure the formation of droplets 236 which will fall downwardly onto a moving conveyor belt 238 trained to run between conveyor wheels 240 and 242 beneath the conduit 232. When the droplets 236 fall onto the conveyor belt 238, they form pellets 244 which harden almost instantaneously and fall off the end of the conveyor 238 into a container 246 which is advantageously filled with water or some other suitable liquid to insure the rapid cooling of each of the pellets. The pellets 244 are then collected from the container 246 and packaged for shipment.

A feature of the invention is the provision for moistening the conveyor belt 238 to insure the rapid formation of the solid polymer scented pellets 244 without sticking to the belt. The belt 238 is advantageously of a material which will not normally stick to a melted polymer but the moistening means 248 insures a sufficiently cold temperature of the belt surface for the adequate formation of the pellets 244. The moistening means comprises a container 250 which is continuously fed with water 252 to maintain a level 254 for moistening the sponge element 256 which bears against the exterior surface of the belt 238.

THE INVENTION

It has now been discovered that novel solid and liquid foodstuff, chewing gum, medicinal products and flavoring compositions having pear, blackberry, peach or apricot flavors with sweet and musky aroma characteristics and sweet and musky flavor characteristics and novel perfume compositions and perfumed articles having sweet, musky, animal-like aromas may be provided by the macrocyclic lactones having the structure:

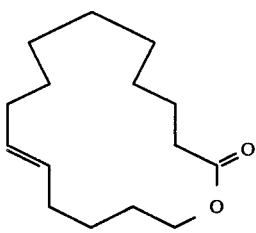

It is to be understood that the structure:

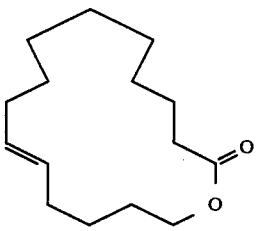

represents a "cis" as well as a "trans" isomer.

The macrocyclic lactones of our invention may be prepared by first reacting the unsaturated alcohol having the structure:

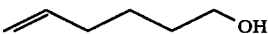

with the ester having the structure:

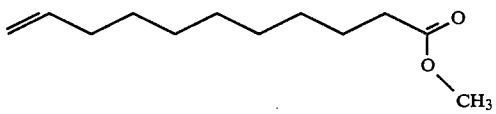

in the presence of an alkali metal alkoxide and a solvent according to the reaction:

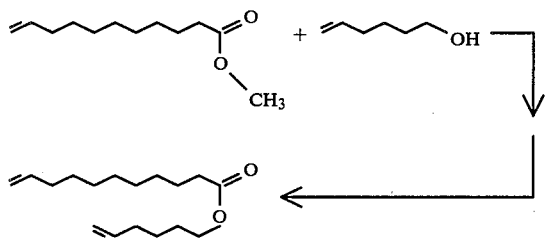

The catalyst used in the reaction may be an alkali metal alkoxide such as sodium methoxide, sodium ethoxide, sodium isopropoxide, sodium t-butoxide, potassium methoxide, potassium ethoxide, potassium isopropoxide and potassium t-butoxide. The solvent used is one which is inert to the reactants as well as inert to the reaction products and, in addition, is one which will not evaporate during the reaction at the desired temperature. The desired temperature of reaction is between about 90° and 140° C. The desired pressure is between about 0.5 atmospheres up to about 10 atmospheres. Accordingly, an appropriate solvent would be toluene, xylene or the like. The most preferred solvent is toluene. The mole ratio of ester having the structure:

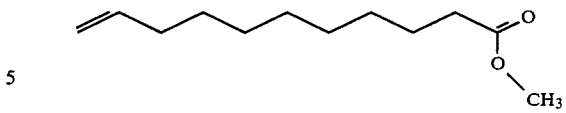

to unsaturated alcohol having the structure:

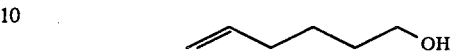

may vary from about 0.5:1 up to about 1:0.5 with a preferred mole ratio of about 1:1. The concentration of alkali metal alkoxide in the reaction mass may vary from about 5 grams per liter up to about 30 grams per liter. The concentration of reactants in the reaction mass may vary from about 2 moles per liter up to about 6 moles per liter.

At the end of the first reaction, the solvent is stripped and the reaction mass is distilled to create a product boiling at about 2.5 mm/Hg pressure at 132°–135° C.

This reaction product is then reacted according to an internal metathesis reaction according to the following reaction:

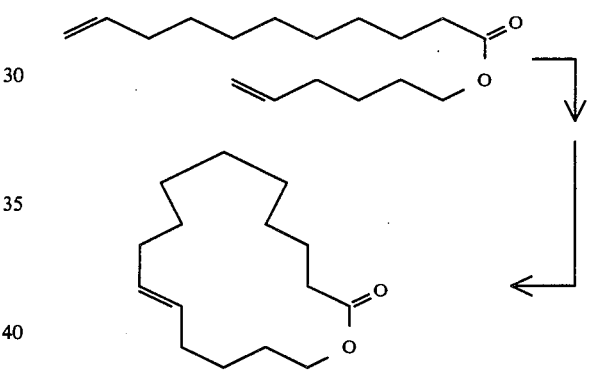

The conditions of this metathesis reaction are set forth in the article by Tsuji and Hashiguchi, Journal of Organometallic Chemistry, 218(1981), 69–80, the disclosure of which is incorporated by reference herein. The reaction is carried out in the presence of catalysts such as $WCl_6$ and $WOCl_4$ as primary catalysts and tetramethyl tin, tetramethyl lead, $Cp_2TiCH_3$ taken twice and $Cp_2ZrCH_3$ taken twice as co-catalysts.

At the end of the reaction, the resulting product having the structure:

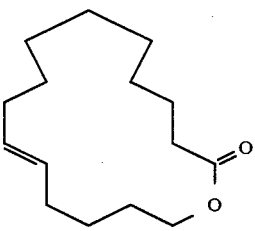

is isolated by means of extraction and distillation. The resulting product may then be separated into its cis and trans isomers by standard preparative chromatographic techniques.

When the macrocyclic lactones of our invention are used as food flavor adjuvants, the nature of the co-ingredients included with said macrocyclic lactones in formulating the product composition will serve to alter the organoleptic characteristics of the ultimate foodstuff treated therewith.

As used herein in regard to flavors, the terms "alter" and "modify" in their various forms means "supplying or imparting flavor character or note to otherwise bland, relatively tasteless substances or augmenting the existing flavor characteristic where a natural flavor or synthetic flavor or mixture of natural and synthetic flavors is deficient in some regard, or supplementing the existing flavor impression to modify its quality, character or taste".

As used herein, the term "enhance" is intended to mean the intensification (without effecting a change in kind of quality or aroma or taste) of one or more taste and/or aroma nuances present in the organoleptic impression of a consumable material, e.g., foodstuff, tobacco, chewing gum, medicinal product, perfume composition or perfumed article.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "chewing gum" is intended to mean a composition which comprises a substantially water-insoluble, chewable plastic gum base such as chicle, or substitutes therefor, including jelutung, guttakay rubber and/or certain comestible natural or synthetic resins or waxes. Incorporated within the gum base, in admixture therewith may be plasticizers or softening agents, e.g., glycerine; and a flavoring composition which incorporates the macrocyclic lactones of our invention, and, in addition, sweetening agents which may be sugars, including sucrose or dextrose and/or artificial sweeteners including dipeptides, cyclamates and saccharin. Other optional ingredients may also be present.

The term "medicinal product" includes both solids and liquids which are ingestible, non-toxic materials having medicinal value such as cough syrups, cough drops, toothpaste, aspirin and chewable medicinal tablets as further exemplified herein.

Substances suitable for use herein as co-ingredients or flavoring adjuvants are well known in the art for such use being extensively described in the relevant literature. Such material is required to be "ingestibly" acceptable and thus non-toxic or otherwise non-deleterious. Particularly critical is the additional requirement that such material be organoleptically compatible with the macrocyclic lactones encompassed within the scope of our invention. Also critical is the additional requirement that such material be nonreactive (within the range of storage conditions and room temperature use conditions) with the macrocyclic lactones.

Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene, (2,6-di-tertiary-butyl-4-methyl phenol), propyl gallate and the like and sequestrants, e.g., citric acid.

Thickener compounds include carriers, binders, protective colloids, suspending agents, emulsifiers, and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates, starches, pectins, and emulsifiers, e.g., mono- and diglycerides of fatty acids, skim silk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents, such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like, firming agents such as aluminum sodium sulfate, calcium chloride and calcium gluconate; texturizers, anti-caking agents, e.g., aluminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, cis and trans 2-methyl-2-pentenoic acid, and cis and trans 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethyl-acrolein, n-hexanal, 2-hexenal, cis-3-hexenal, 2-heptenal, 4-(p-hydroxyphenyl)-2-butanone, alpha-ionone, beta-ionone, methyl-3-butanone, 2-pentanone, 2-pentenal and propanal; alcohols such as 1-butanol, benzyl alcohol, 1-borneol, trans-3-buten-1-ol, ethanol, geraniol, 1-hexanol, 2-heptenol-1, trans-3-hexenol-1, cis-3-hexen-1-ol, 3-methyl-3-buten-1-ol, 1-penten-2-ol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, n-hexyl butyrate, isoamyl acetate, isopropyl butyrate, methyl acetate, methyl-n-butyrate, methyl caproate, methyl isobutyrate, alpha-methyl-n-butyrate, n-propyl acetate, n-amyl acetate, n-amyl-n-butyrate, benzyl salicylate, dimethyl anthranilate, ethyl methylphenylglycidate, ethyl succinate, isobutyl cinnamate, and terpenyl acetate; lactones, such as delta-decalactone, delta-undecalactone, deltanonyl-lactone, gamma-undecalactone, gamma-dodecalactone and gamma nonyl-lactone as well as "peach" lactones; essential oils, such as jasmine absolute, rose absolute, orris absolute, lemon essential oil, Bulgarian rose, yara yara, natural raspberry oil and vanilla; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff whether simulated or natural, and should, in any event, be capable of providing an environment in which the macrocyclic lactones can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g. simulated foodstuffs, ingredients capable of providing normally solid compositions should be selected such as various cellulose derivatives.

As will be appreciated by those skilled in the art, the amount of the macrocyclic lactones employed in a particular substance can vary over a relatively wide range whereby specific desired organoleptic effects (having particular reference to the nature of the product) are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e. sufficient to alter, modify or enhance the organoleptic characteristics of the parent composition, whether foodstuff per se or flavoring composition.

The use of insufficient quantities of the macrocyclic lactones will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it has been found that quantities of the macrocyclic lactones ranging from a small but effective amount, e.g. 0.0001 parts per million up to about 50 parts per million by weight based on total composition are suitable. Concentrations in excess of the maximum quantity stated are not normally recommended since they fail to provide commensurate enhancement or augmentation of organoleptic properties. In those instances wherein the macrocyclic lactones are added to the foodstuff as an integral component of a flavoring composition, it is, of course, essential that the total quantity of flavoring composition employed be sufficient to yield an effective concentration (of macrocyclic lactones) in the foodstuff product.

Food flavoring compositions prepared in accordance with the present invention preferably contain the macrocyclic lactones in concentrations ranging from about 0.01% up to about 15% by weight based on the total weight of the said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the macrocyclic lactones with, for example, gum arabic, gum tragacanth, carrageenan and the like, and thereafter spray-drying the resultant mixture whereby to obtain the particulate solid product. Pre-prepared flavor mixes in powder form, e.g. a fruit-flavored powder mix are obtained by mixing the dried solid components, e.g. starch, sugar and the like, and the macrocyclic lactones in a dry blender until the requisite degree of uniformity is achieved.

It is presently preferred to combine with the macrocyclic lactones, the following adjuvants:

p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
β-Damascone;
β-Damascenone;
Ethyl butyrate;
Acetic acid;
n-Hexyl acetate;
n-Hexyl isobutyrate;
Trans-2-hexenal;
Linalyl isobutyrate;
n-Hexyl-2-methyl-n-butyrate;
Gamma-undecalactone;
Gamma-nonalactone;
Gamma decalactone;
Delta undecalactone;
Delta dodecalactone;
Delta nonyl lactone;
"Peach" lactone;
Naphthyl ethyl ether;
Diacetyl;
Apple Fusel Oil;
Sauge Sclaree;
Coriander Oil;
Ethyl acetate;
Anethole;
Isoamyl-n-butyrate;
Ethyl-2-methyl-cis-3-pentenoate;
Cis-3-hexenol-1;
2-Methyl-cis-3-pentenoic acid;
2-Methyl-2-pentenoic acid;
Elemecine(4-allyl-1,2,6-trimethoxy benzene);
Isoelemecine(4-propenyl-1,2,6-trimethoxy benzene); and
2-(4-hydroxy-4-methylpentyl)norbornadiene prepared according to U.S. Pat. No. 3,886,289.

The macrocyclic lactones and one or more auxiliary perfume ingredients, including, for example, alcohols, aldehydes, nitriles, esters, cyclic esters, ketones and natural essential oils, may be admixed so that the combined odors of the individual components produce a pleasant and desired fragrance particularly and preferably in musk and "animal-like" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to its particular olfactory characteristics, but the over-all effect of the perfume composition will be the sum of the effects of each of the ingredients. Thus, the macrocyclic lactones can be used to alter the aroma characteristics of a perfume composition, for example, by utilizing or moderating the olfactory reaction contributed by at least one other ingredient in the composition.

The amount of the macrocyclic lactones of our invention which will be effective in perfume compositions depends on many factors, including the other ingredients, their amounts and the effects which are desired. It has been found that perfume compositions containing as little as 0.01% of the macrocyclic lactones and even less (e.g. 0.005%) can be used to impart rich, animal-musk and sweet notes to soaps, anionic, cationic, nonionic and zwitterionic detergents, fabric softener articles, perfumed polymers, cosmetics and other products. The amount employed can range up to 10% of the fragrance components and will depend on considerations of cost, nature of the end product, the effect desired on the finished product and the particular fragrance sought.

The macrocyclic lactones are useful, taken alone or in perfume compositions as olfactory components in anionic, cationic and nonionic detergents, soaps, fabric softener compositions and fabric softener articles for use in clothes driers (e.g. "BOUNCE" ®, a registered trademark of the Procter & Gamble Company of Cincinnati, Ohio), space odorants and deodorants, perfumes, colognes, toilet water, bath preparations, such as bath oils, and bath solids; hair preparations such as lacquers, brilliantines, creams, deodorants, hand lotions and sun screens, powders such as talcs, dusting powders, face powders and the like. When used as an olfactory component in perfume compositions or perfumed articles, such as anionic, cationic and nonionic detergents and in fabric softener compositions and fabric softener articles (e.g. for use in clothing driers) as little as 0.05% of the macrocyclic lactones of our invention will suffice to impart rich, animal-musk and sweet notes. Generally no more than 5% of the macrocyclic lactones based on the ultimate end product is required in the perfume composition or in the perfumed article.

In addition, the perfume composition or fragrance composition of our invention can contain a vehicle or carrier for the macrocyclic lactones. The vehicle can be a liquid such as a non-toxic alcohol, a non-toxic glycol, or the like. The carrier can also be an absorbent solid such as a gum (e.g. gum arabic) or components for encapsulating the composition (such as gelatin) as by means of coacervation.

The macrocyclic lactones of our invention may be blended into polymers when forming a perfumed polymer by means of extrusion using a single or double screw extruder or technique such as that set forth in U.S. Pat. No. 4,247,498 issued on Jan. 27, 1981, the disclosure of which is incorporated by reference herein, which discloses microporous polymers which are capable of containing volatile substances such as perfumes and the like and forms ranging from films to blocks and intricate shapes from synthetic thermoplastic polymers such as olefinic condensation or oxidation polymers. Other techniques of blending the macrocyclic lactones of our invention with polymers are exemplified in U.S. Pat. No. 3,505,432 (the specification for which is incorporated by reference herein) which discloses a method for scenting a polyolefin with such materials as the macrocyclic lactones of our invention which comprises:

(a) mixing a first amount of the liquid polyolefin (e.g. polyethylene or polypropylene) with a relatively large amount of scent-imparting material (in this case the macrocyclic lactones of our invention) to form a flowable mass;

(b) forming drops of said mass and causing substantially instantaneous solidification of said drops into polyolefin pellets having a relatively large amount of such scent-imparting materials as the macrocyclic lactones of our invention imprisoned therein;

(c) melting said pellets with a second amount of polyolefin and said second amount being larger than the first amount; and (d) solidifying the melt of (c).

The following Examples I and II set forth techniques for preparing the macrocyclic lactones of our invention. The examples following Example II, Examples III, et seq. indicate organoleptic uses of the macrocyclic lactones of our invention.

All parts and percentages given herein are by weight unless otherwise specified.

EXAMPLE I

PREPARATION OF DEHYDROEXALTOLIDE INTERMEDIATE

Reaction:

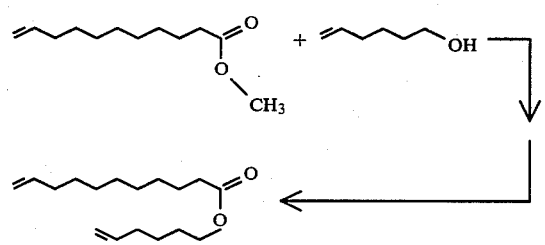

Into a one liter flask equipped with stirrer, thermometer, Vigreux column and reflux head and nitrogen blanket apparatus are placed 200 grams (2 moles) of 5-hexenol-1, 396 grams (2 moles) of methyl-10-undecylenate, 12.5 grams of sodium methoxide and 250 ml toluene.

The resulting mixture is heated to reflux and the methanol reaction product is distilled off via a short column with reflux head. The distillation of the methanol continues until the vapor temperature remains at 105°–110° C. and the liquid temperature remains at 145°–150° C.

The reaction mass is acidified with aqueous acetic acid and washed with water. The toluene is stripped off and the resulting product is then distilled through a 14" Vigreux column with reflux head yielding 460 grams of product (desired boiling point 132°–135° C. at 2.5 mm/Hg). The distillation product contains the following fractions:

| Fraction Number | Vapor Temp. (°C.) | Liquid Temp. (°C.) | Vacuum mm/Hg | Weight of Fraction (grams) |
|---|---|---|---|---|
| 1 | 66/65 | 144/152 | 2.5/2.5 | 3.7 |
| 2 | 125 | 144 | 2.4 | 13.0 |
| 3 | 126 | 148 |  | 22.1 |
| 4 | 131 | 149 | 3.0 | 31.4 |
| 5 | 130 | 149 | 2.4 | 34.9 |
| 6 | 132 | 140 | 3.0 | 35.9 |
| 7 | 134 | 150 | 2.4 | 41.8 |
| 8 | 136 | 151 | 2.6 | 34.3 |
| 9 | 137 | 152 | 2.7 | 41.6 |
| 10 | 146 | 156 | 2.9 | 44.7 |
| 11 | 147 | 157 | 4.2 | 29.9 |
| 12 | 148 | 158 | 6.0 | 22.8 |
| 13 | 131 | 152 | 2.5 | 40.6 |
| 14 | 132 | 158 | 2.5 | 38.5 |
| 15 | 135 | 168 | 2.5 | 27.2 |
| 16 | 151 | 190 | 2.5 | 15.5 |
| 17 | 75 | 220 | 2.5 | 5.3 |

Figure 1:
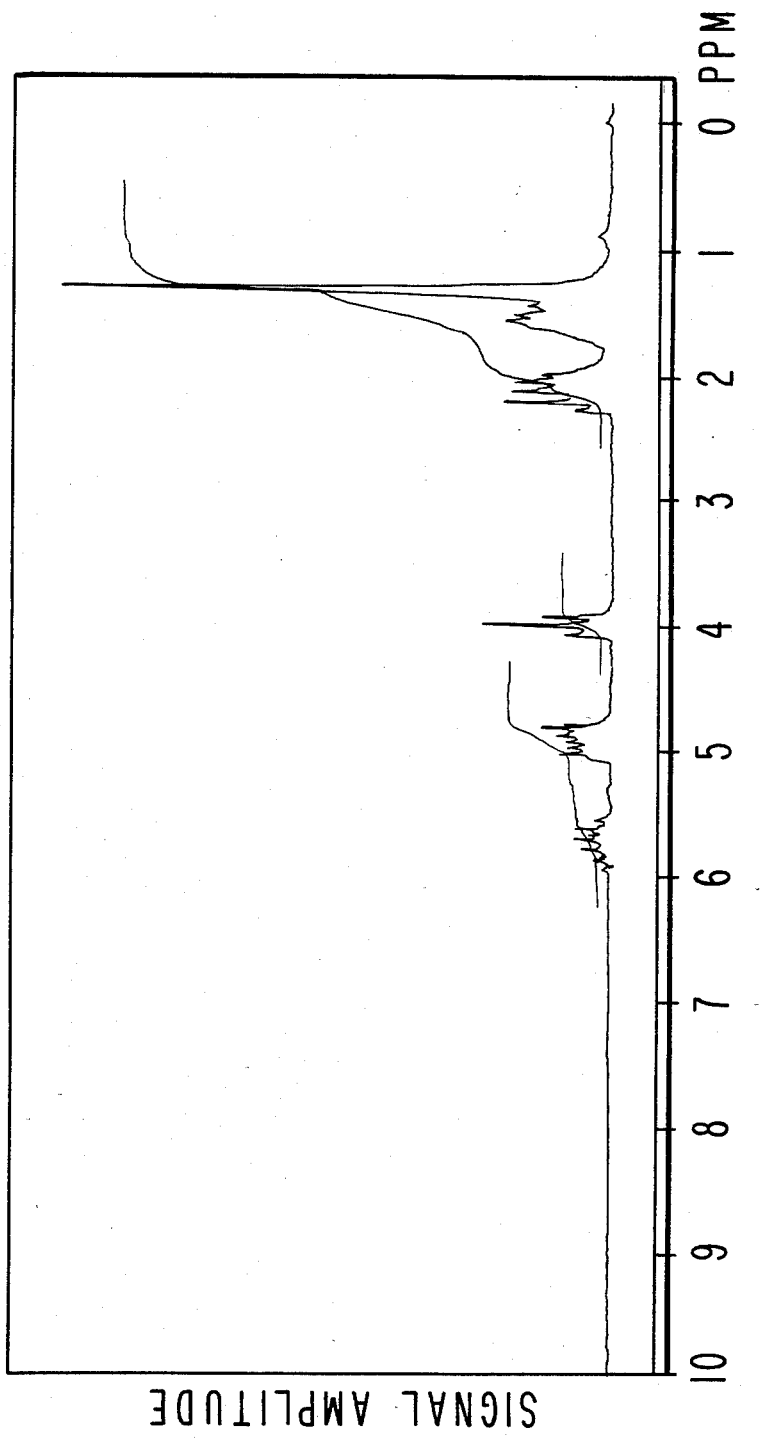
FIG. 1 is the NMR spectrum for the compound produced according to Example I having the structure.

FIG. 1 is the NMR spectrum for the compound having the structure:

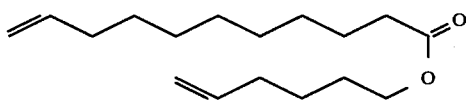

(conditions: Field Strength: 100 MHz; Solvent: CFCl$_3$).

FIG. 2 is the infra-red spectrum for the compound having the structure:

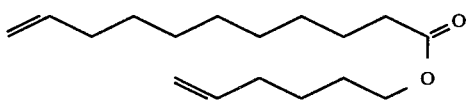

Fractions 6–15 are bulked and used in Example II.

EXAMPLE II

PREPARATION OF DEHYDROEXALTOLIDE

Reaction:

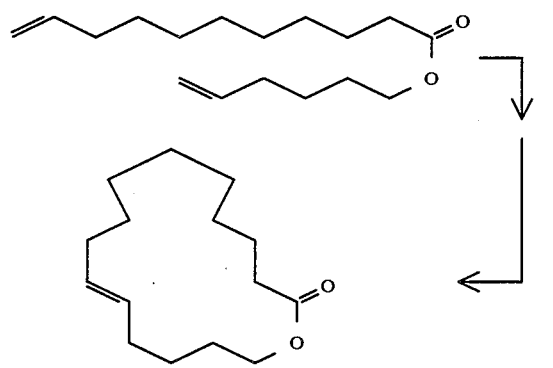

100 ml anhydrous chlorobenzene and 478.2 mg of tungsten hexachloride are mixed under nitrogen blanked for 30 minutes. 6.6 grams of 5-hexenyl-10-undecylenate prepared according to Example I are added to the reaction mass under a nitrogen blanket. The reaction mass is stirred at 40° C. for 30 minutes. 525 microliters of tetramethyl tin are then added to the reaction mass with stirring. The reaction mass is stirred for 60 minutes at 40° C. The resulting mixture is added over a 3 hour period to 300 ml of monochlorobenzene. The resulting mixture is heated to 80°–90° C. for 3–4 hours and then aged for 7 hours. To the reaction mixture 400 microliters of tetramethyl tin is added and over a period of 2–3 hours, a solution of 371 mg of tungsten hexachloride dissolved in 100 ml chlorobenzene is added to the reaction mass at 85°–90° C. The reaction mass is aged for 7 hours (conversion: 45%).

An additional 350 microliters of tetramethyl tin is added to the reaction mass and dropwise over a 2–3 hour period, 307 mg of tungsten hexachloride in 100 ml chlorobenzene is added to the reaction mass at 85°–90° C. The reaction mass is aged for 7 hours (conversion: 95%).

The reaction mass is stirred with water for 30 minutes and washed with 4 volumes of water.

The chlorobenzene is stripped off leaving 5.44 grams of oil. The reaction product is then distilled at 1.8 mm/Hg at 130°–135° C. The resulting product is then chromatographed and by means of preparative column chromatography, the cis isomer is separated from the trans isomer.

FIG. 3 is the GLC profile for the reaction product prior to distillation of Example II. The peak indicated by reference numeral "31" is the peak for the starting material having the structure:

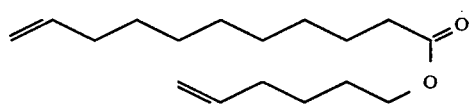

The peak indicated by reference numeral "32" is the peak for the trans isomer of the compound having the structure:

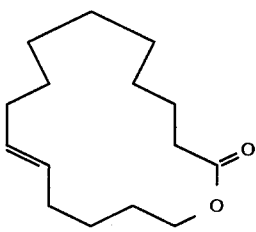

The peak indicated by reference numeral "33" is the peak for the cis isomer having the structure:

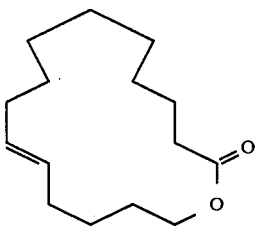

(GLC conditions: 10'×0.25" 10% Carbowax column programmed at 150°–225° C. at 8° C. per minute).

FIG. 4 is the NMR spectrum for the trans isomer of the compound having the structure:

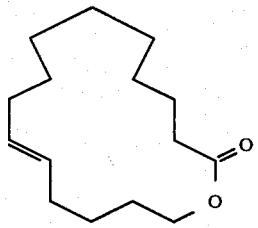

(conditions: Field Strength: 100 MHz; Solvent: CFCl$_3$).

FIG. 5 is the infra-red spectrum for the trans isomer of the compound having the structure:

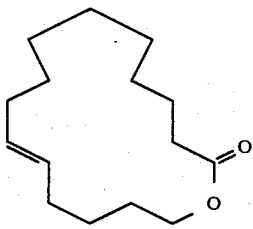

FIG. 6 is the NMR spectrum for the cis isomer of the compound having the structure:

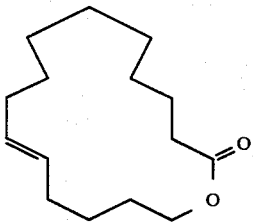

(conditions: Field Strength: 100 MHz; Solvent: CFCl$_3$).

FIG. 7 is the infra red spectrum for the cis isomer of the compound having the structure:

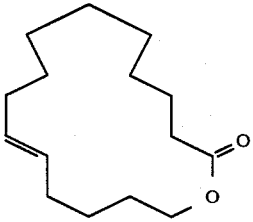

EXAMPLE III

MUSK PERFUME FORMULATION

The following musk perfume formulation is prepared:

| Ingredients | Parts by Weight |
|---|---|
| Musk ambrette | 200 |

-continued

| Ingredients | Parts by Weight |
|---|---|
| Musk ketone | 200 |
| Beta ionone | 50 |
| Vetiveryl acetate | 50 |
| Sandalwood oil | 100 |
| Benzyl benzoate | 400 |
| Mixture of cis and trans isomers having the structure: 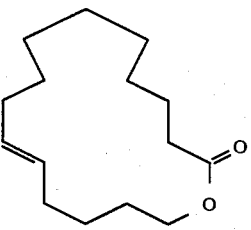 prepared according to Example 2 | 20 | in Example 23.

The mixture of compounds having the structure:

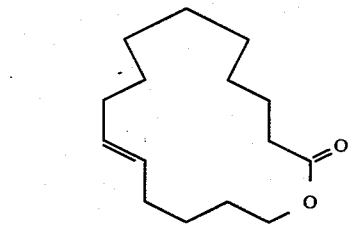

imparts to this musk formulation a natural "animal musk", sweet, tonka-like and coumarin-like aroma causing it to be more natural-like. Accordingly, this formulation can be described as "musky, with animal-like, sweet and coumarin-line undertones".

EXAMPLE IV

PREPARATION OF COSMETIC POWDER COMPOSITIONS

Cosmetic powder compositions are preapred by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| Mixture of "cis" and "trans" isomers having the structure: 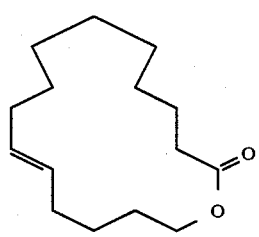 | A sweet, jusky, animalic, tonka-like and coumarin-like aroma. |
| Perfume composition of Example III. | Musky with animal-like, sweet and coumarin-like undertones. |

TABLE I-continued

| Substance | Aroma Description |
|---|---|
| "Cis" isomer of the compound having the structure: | A sweet, musky, animal-like, tonka-like and coumarin-like aroma. |
| "Trans" isomers of the compound having the structure: | A sweet, musky, animalic tonka-like and coumarin-like aroma. |

EXAMPLE V

PERFUMED LIQUID DETERGENTS

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table I of Example IV, are prepared containing 0.10%, 0.15%, 0.20%, 0.25%, 0.30% and 0.35% of the substance set forth in Table I of Example IV. They are prepared by adding and homogeneously mixing the appropriate quantity of substance set forth in Table I of Example IV in the liquid detergent. The detergents all possess excellent aromas as set forth in Table I of Example IV, the intensity increasing with greater concentrations of substance as set forth in Table I of Example IV.

EXAMPLE VI

PREPARATION OF COLOGNES AND HANDKERCHIEF PERFUMES

Compositions are set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handkerchief perfumes at all levels indicated.

EXAMPLE VII

PREPARATION OF SOAP COMPOSITIONS

One hundred grams of soap chips (per sample) (IVORY ®, produced by the Procter & Gamble Company of Cincinnati, Ohio), are each mixed with one gram samples of substances as set forth in Table I of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example IV.

EXAMPLE VIII

PREPARATION OF SOLID DETERGENT COMPOSITIONS

Detergents are prepared using the following ingredients according to Example I of Canadian Pat. No. 1,007,948 (incorporated by reference herein):

| Ingredient | Percent by Weight |
|---|---|
| "Neodol ® 45-11" (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE IX

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
1. a water "dissolvable" paper ("Dissolvo paper")
2. Adogen 448 (m.p. about 140° F.) as the substrate coating; and
3. an outer coating having the following formulation (m.p. about 150° F.):
   57% $C_{20-22}$ HAPS
   22% isopropyl alcohol
   20% antistatic agent
   1% of one of the substances as set forth in Table I of Example IV.

Fabric softening compositions prepared according to Example I at column 15 of U.S. Pat. No. 3,632,396 having aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener nonwoven fabrics and these aroma characteristics are described in Table I of Example IV, supra.

EXAMPLE X

HAIR SPRAY FORMULATIONS

The following hair spray formulation is prepared by first dissolving PVP/VA E-735 co-polymer manufactured by the GAF Corporation of 140 West 51st Street, New York, N.Y. in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example IV, supra | 0.10 weight percent |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE XI

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat® 755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting Composition A and Composition B are then mixed in a 50:50 weight ratio of A:B and cooled to 45° C. and 0.3 weight percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

EXAMPLE XII

Scented polyethylene pellets having a pronounced scent as set forth in Table I of Example IV are prepared as follows:

75 pounds of polyethylene of a melting point of about 220° F. are heated to about 230° F. in a container of the kind illustrated in FIGS. 8 and 9. 25 Pounds of each of the perfume materials of Table I of Example IV supra, are then added quickly to the liquified polyethylene. The lid 228 is put in place and the agitating means 273 are actuated. The temperature is maintained at about 225° F. and the mixing is then continued for about 5–15 minutes. The valve 230 is then opened to allow flow of the molten polyethylene enriched with each of the aroma substance-containing materials to exit through the orifices 234. The liquid falling through the orifices 234 solidify almost instantaneously upon impact with the moving, cooled conveyor 238. Solid polyethylene beads or pellets 244 having pronounced aromas as set forth in Table I of Example IV supra are then formed. Analysis demonstrates that the pellets contain about 25% of each of the perfume substances of Table I of Example IV so that almost no losses of the scenting substance occur. These pellets may be called master pellets.

50 pounds of the scent-containing master pellets are then added to 1,000 pounds of unscented polyethylene powder and the mass is heated to the liquid state. The liquid is molded into thin sheets or films. The sheets or films have a pronounced aroma as set forth in Table I of Example IV supra. The sheets are also fabricated into garbage bags which have aromas as set forth in Table I of Example IV supra.

EXAMPLE XIII

The following basic mangoflavor formulation is prepared:

| Ingredients | Parts by Weight |
|---|---|
| Vanillin | 2.0 |
| Hexyl Acetate | 8.0 |
| Hexyl Isobutyrate | 20.0 |
| Trans-2-hexenal (10% in propylene glycol) | 2.0 |
| β-Caryophyllene | 8.2 |
| 1-Methyl-3-n-propyl-2,4-oxathiane | 32.0 |
| 1-Ethyl-3-n-propyl-4,2-oxathiane | 2.5 |
| 1-Methyl-3-isopropyl-2,4-oxathiane | 3.8 |
| Mango skin extract ex Venezuela | 14.5 |
| n-Hexanal | 0.5 |
| Apple Fusel Oil | 10.0 |
| Linalyl Isobutyrate | 0.5 |
| Hexyl-2-methylbutyrate | 10.0 |
| Sauge Sclaree (10% in propylene glycol) | 0.5 |
| Coriander Oil | 0.5 |
| Food grade ethyl alcohol (aqueous, 95%) | 146.0 |
| Propylene glycol | 800.0 |

To a portion of the above basic mango formulation 0.02% by weight of a cis:trans mixture of the compound having the structure:

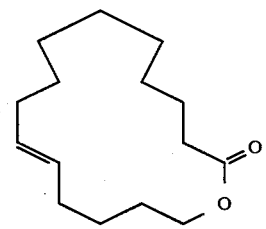

is added. To another portion of the basic mango formulation nothing is added. Both flavor formulations are compared at the rate of 50 ppm in water and evaluated by a blind bench panel of four experienced tasters. All of the tasters of the bench panel state that the flavor containing the mixture of "cis" and "trans" isomers of the compound having the structure:

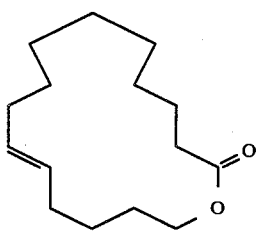

has a more natural, riper mango character. This mango character is enhanced and longer lasting as a result of the addition of the mixture of "cis" and "trans" isomers of the compound having the structure:

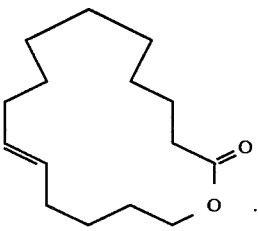

Therefore, the flavor formulation containing the mixture of "cis" and "trans" isomers of the compound having the structure:

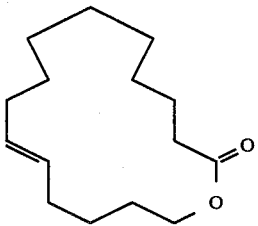

is unanimously preferred.

EXAMPLE XIV

A. POWDER FLAVOR

Twenty grams of the flavor composition of Example XIII which flavor composition contains a mixture of cis and trans isomers of the compound having the structure:

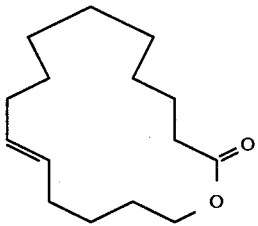

prepared according to Example II is emulsified in a solution containing 300 grams gum acacia and 700 grams water. The emulsion is spray-dried with a Bowen Lab Model Drier utilizing 250 c.f.m. of air with an inlet temperature of 500° F. and outlet temperature of 200° F. and a wheel speed of 50,000 r.p.m.

B. PASTE BLEND

| The following mixture is then prepared: | |
|---|---|
| Ingredients | Parts by Weight |
| Liquid flavor composition of Example XIII | 48.4 |
| Cab-O-Sil M-5 (Brand of Silica produced by the Cabot Corporation of 125 High Street, Boston, Mass. 02110); Physical properties: Surface area: 200 m²/gm Nominal particle Size: 0.012 microns Density: ⅜ lbs./cu.ft. | 3.2 |

The Cab-O-Sil is dispersed in the liquid flavor composition with vigorous stirring, thereby resulting in a viscous liquid. 48.4 parts by weight of the powder flavor composition prepared in Part A is then blended into the said viscous liquid with stirring at 25° C. for a period of 30 minutes, resulting in a thixotropic sustained released flavor paste.

EXAMPLE XV

CHEWING GUM 100 parts by weight of chicle are mixed with 4 parts by weight of the flavor prepared in accordance with Example XIVB. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long-lasting mango flavor.

EXAMPLE XVI

TOOTHPASTE FORMULATION

The following separate groups of ingredients are prepared:

| | |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium n-Lauroyl Sarcosinate (foaming agent) |
| Group "D" | |
| 1.200 | Flavor Material of Example XIVB |
| 100.00 (Total) | |

PROCEDURE

1. To ingredients in Group "A" are stirred and heated in a steam jacketed kettle to 160° F.
2. Stirring is continued for an additional three to five minutes to form a homogeneous gel.

3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant mango flavor of constant strong intensity throughout said procedure (1–1.5 minutes).

EXAMPLE XVII

CHEWABLE VITAMIN TABLETS

The flavor material produced according to the process of Example XIVB is added to a chewable vitamin tablet formulation at a rate of 5 gm/kg which chewable vitamin tablet formulation is prepared as follows:

| Ingredients | Gms/1000 Tablets |
| --- | --- |
| Vitamin C (ascorbic acid) | 70.0 |
| as ascorbic acid-solution mixture 1:1 | |
| Vitamin $B_1$ (thiamine mononitrate) | 4.0 |
| as Rocoat ® thiamine mononitrate 33% (Hoffman La Roche) | |
| Vitamin $B_2$ (riboflavin) | 5.0 |
| as Rocoat ® riboflavin 33⅓% | |
| Vitamin $B_6$ (pyridoxine hydrochloride) | 4.0 |
| as Rocoat ® pyridoxide hydrochloride 33⅓% | |
| Niacinamide | 33.0 |
| as Rocoat ® niacinamide 33⅓% | |
| Calcium pantothenate | 11.5 |
| Vitamin $B_{12}$ (cyanocobalamin) | 3.5 |
| as Merck 0.1% in gelatin | |
| Vitamin E (dl-alpha tocopheryl acetate) | 6.6 |
| as dry Vitamin E acetate 33⅓% Roche | |
| d-Biotin | 0.044 |
| Certified lake color | 5.0 |
| Flavor of Example XIVB | 2.5 |
| Sweetener-sodium saccharin | 1.0 |
| Magnesium stearate lubricant | 10.0 |
| Mannitol q.s. to make | 500.0 |

Preliminary tablets are prepared by slugging, with flatfaced punches and grinding the slugs to 14 mesh. 13.5 grams dry Vitamin A acetate and 0.6 grams Vitamin D are then added as beadlets. The entire blend is then compressed using concave punches at 0.5 grams each.

Chewing of the resultant tablet yields a pleasant, long-lasting, consistently strong mango flavor for a period of 12 minutes.

What is claimed is:

1. A process for augmenting or enhancing the aroma of a perfume polymer comprising the step of intimately admixing with a polymer, an aroma augmenting or enhancing quantity of a "cis" or "trans" isomer or a mixture of "cis" and "trans" isomers of the compound defined according to the structure:

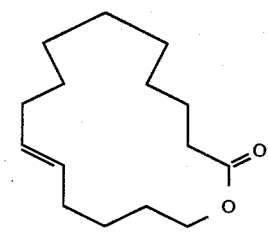

* * * * *